United States Patent
Baturin et al.

(10) Patent No.: US 10,096,098 B2
(45) Date of Patent: Oct. 9, 2018

(54) PHASE RETRIEVAL FROM DIFFERENTIAL PHASE CONTRAST IMAGING

(71) Applicant: Carestream Health, Inc., Rochester, NY (US)

(72) Inventors: Pavlo Baturin, Rochester, NY (US); Richard A. Simon, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 682 days.

(21) Appl. No.: 14/143,183

(22) Filed: Dec. 30, 2013

(65) Prior Publication Data

US 2015/0187096 A1    Jul. 2, 2015

(51) Int. Cl.
| | | |
|---|---|---|
| G06T 5/00 | (2006.01) | |
| G06T 5/50 | (2006.01) | |
| G01T 1/164 | (2006.01) | |
| A61B 6/00 | (2006.01) | |

(52) U.S. Cl.
CPC ............... *G06T 5/50* (2013.01); *A61B 6/484* (2013.01); *A61B 6/5258* (2013.01); *G01T 1/164* (2013.01); *G06T 5/002* (2013.01); *A61B 6/4035* (2013.01); *A61B 6/4291* (2013.01); *A61B 6/5205* (2013.01); *G06T 2207/10116* (2013.01)

(58) Field of Classification Search
None
See application file for complete search history.

(56) References Cited

U.S. PATENT DOCUMENTS

| | | |
|---|---|---|
| 5,812,629 A | 9/1998 | Clauser |
| 6,560,309 B1 | 5/2003 | Becker et al. |
| 7,346,204 B2 | 3/2008 | Ito |
| 7,453,981 B2 | 11/2008 | Baumann et al. |
| 7,639,786 B2 | 12/2009 | Baumann et al. |
| 7,646,843 B2 | 1/2010 | Popescu et al. |
| 7,693,256 B2 | 4/2010 | Brahme et al. |
| 7,817,777 B2 | 10/2010 | Baumann et al. |
| 8,280,000 B2 | 10/2012 | Takahashi |

(Continued)

FOREIGN PATENT DOCUMENTS

| | | |
|---|---|---|
| CN | 101257851 | 9/2008 |
| CN | 101952900 | 1/2011 |

(Continued)

OTHER PUBLICATIONS

Compact X-ray Grating Interferometry for Phase and Dark-field Computer Tomography in the Diagnostic Energy Range. Thomas Thuring. Nov. 2013.*

(Continued)

*Primary Examiner* — Delomia L Gilliard

(57) ABSTRACT

Embodiments of methods and apparatus are disclosed for obtaining differential phase contrast imaging system and methods for same. Method and apparatus embodiments can provide regularized phase contrast retrieval that can address noise reduction and/or edge enhancement. Certain exemplary embodiments can suppress stripe artifacts occurring in the process of integration of noisy differential phase data. Further, certain exemplary embodiments can use transmission images and/or dark-field images to improve or restore phase contrast images affected by noise edges.

20 Claims, 7 Drawing Sheets

(56) References Cited

U.S. PATENT DOCUMENTS

| | | | |
|---|---|---|---|
| 8,515,002 B2 | 8/2013 | Huang et al. | |
| 8,855,395 B2 | 10/2014 | Baturin et al. | |
| 9,001,967 B2 | 4/2015 | Baturin et al. | |
| 9,357,975 B2 | 6/2016 | Baturin et al. | |
| 9,494,534 B2 | 11/2016 | Baturin et al. | |
| 2009/0220832 A1 | 9/2001 | Ning et al. | |
| 2005/0249328 A1 | 11/2005 | Bruder et al. | |
| 2007/0183560 A1* | 8/2007 | Popescu | A61B 6/032 378/5 |
| 2007/0183582 A1 | 8/2007 | Baumann et al. | |
| 2007/0183583 A1 | 8/2007 | Baumann et al. | |
| 2007/0014643 A1 | 1/2008 | Bjorkholm et al. | |
| 2008/0009717 A1 | 1/2008 | Herrmann et al. | |
| 2008/0075228 A1 | 3/2008 | Tasaki | |
| 2008/0123805 A1 | 5/2008 | Zellerhoff | |
| 2008/0273653 A1 | 11/2008 | Niwa et al. | |
| 2008/0092227 A1 | 4/2009 | David et al. | |
| 2009/0097730 A1 | 4/2009 | Kasai et al. | |
| 2009/0116720 A1 | 5/2009 | Ritman | |
| 2010/0220834 A1 | 9/2010 | Heismann et al. | |
| 2010/0246764 A1 | 9/2010 | Itoh et al. | |
| 2010/0246765 A1 | 9/2010 | Murakoshi et al. | |
| 2010/0272235 A1 | 10/2010 | Takahashi | |
| 2011/0085639 A1 | 4/2011 | Nakamura et al. | |
| 2011/0135057 A1 | 6/2011 | Mori et al. | |
| 2011/0206181 A1 | 8/2011 | Linev | |
| 2011/0243305 A1 | 10/2011 | Tada | |
| 2012/0020461 A1 | 1/2012 | Roessl et al. | |
| 2012/0045108 A1 | 2/2012 | Shechter | |
| 2012/0057677 A1 | 3/2012 | Vogtmeier et al. | |
| 2012/0093284 A1 | 4/2012 | Takemoto et al. | |
| 2012/0114098 A1 | 5/2012 | Mikami et al. | |
| 2012/0163554 A1 | 6/2012 | Tada | |
| 2012/0250972 A1* | 10/2012 | Tada | A61B 6/4291 382/132 |
| 2013/0010926 A1 | 1/2013 | Tada | |
| 2013/0028378 A1 | 1/2013 | Stutman et al. | |
| 2013/0108015 A1 | 5/2013 | Kottler et al. | |
| 2013/0156284 A1 | 6/2013 | Koehler et al. | |
| 2013/0259194 A1 | 10/2013 | Yip et al. | |
| 2013/0308750 A1 | 11/2013 | Ishii | |
| 2014/0044234 A1* | 2/2014 | Hashimoto | A61B 6/4291 378/62 |
| 2014/0177789 A1 | 6/2014 | Baturin et al. | |
| 2014/0185746 A1 | 7/2014 | Baturin et al. | |
| 2014/0185896 A1 | 7/2014 | Baturin et al. | |
| 2014/0226782 A1 | 8/2014 | Stutman et al. | |
| 2014/0226783 A1 | 8/2014 | Ning et al. | |
| 2014/0226785 A1 | 8/2014 | Stutman et al. | |
| 2014/0270060 A1 | 9/2014 | Date et al. | |
| 2014/0270061 A1 | 9/2014 | Yamaguchi | |
| 2014/0286477 A1 | 9/2014 | Ishii et al. | |
| 2014/0341347 A1 | 11/2014 | Radicke | |
| 2014/0355740 A1 | 12/2014 | Koehiler et al. | |
| 2015/0092916 A1 | 4/2015 | Baturin et al. | |
| 2015/0110247 A1 | 4/2015 | Baturin et al. | |
| 2015/0117599 A1 | 4/2015 | Yun et al. | |
| 2015/0131777 A1* | 5/2015 | Makifuchi | A61B 6/4291 378/36 |
| 2015/0182178 A1 | 7/2015 | Baturin et al. | |
| 2015/0187096 A1 | 7/2015 | Baturin et al. | |
| 2015/0216499 A1 | 8/2015 | Martens et al. | |
| 2016/0038107 A1 | 2/2016 | Baturin et al. | |
| 2016/0095562 A1 | 4/2016 | Baturin et al. | |
| 2016/0125599 A1* | 5/2016 | Stampanoni | A61B 6/483 382/131 |

FOREIGN PATENT DOCUMENTS

| | | |
|---|---|---|
| CN | 102197303 | 9/2011 |
| CN | 102325498 | 1/2012 |
| CN | 102639059 | 8/2012 |
| CN | 102802529 | 11/2012 |
| DE | 102006015356 | 8/2007 |
| EP | 1731099 | 12/2006 |
| JP | 2007-203074 | 8/2007 |
| JP | 2011-504395 | 2/2011 |
| JP | 2011-078669 | 4/2011 |
| JP | 2012-090945 | 5/2012 |
| JP | 2012-125343 | 7/2012 |
| JP | 2013-138836 | 7/2013 |
| JP | 2013-536723 | 9/2013 |
| JP | 2013-255536 | 12/2013 |
| JP | 2012-005820 | 4/2014 |
| JP | 2015-519091 | 7/2015 |
| JP | 2016-501630 | 1/2016 |
| WO | 2011/122715 | 10/2011 |
| WO | WO 2012/029048 A1 | 3/2012 |
| WO | WO 2012/080125 | 6/2012 |
| WO | 2013/126296 | 8/2013 |
| WO | 2013/148010 | 10/2013 |
| WO | 2013/187150 | 12/2013 |
| WO | 2014/137318 | 9/2014 |

OTHER PUBLICATIONS

Thomas Turing, et al., Non-linear regularized phase retrieval for unidirectional X-ray differential phase contrast radiography, Optics Express, vol. 19, Issue 25, pp. 25545-25558, Optical Society of America 2011, issn: 10944087.

Thomas Thüring, "Compact X-ray grating interferometry for phase and dark-field computed tomography in the diagnostic energy range," ETH Zurich, PhD Dissertation No. 21321, Nov. 26, 2013, XP055179280, 181 pages.

International Search Report dated Apr. 28, 2015 for International Application No. PCT/US2014/066033, 3 pages.

International Search Report, International application No. PCT/US2016/062389, dated Feb. 2, 2017, 2 pages.

Jian Fu, et al., Helical differential X-ray phase-contrast computed tomography, Physica Medica, vol. 30, pp. 374-379, 2014.

International Search Report, International application No. PCT/US2014/066027, dated May 2, 2015, 2 pages.

International Search Report, International application No. PCT/US2013/026301, dated Jun. 3, 2013, 3 pages.

International Search Report, International application No. PCT/US2013/075898, dated Apr. 22, 2014, 2 pages.

Supplementary European Search Report, dated Nov. 27, 2015, European Application No. 13769560.7, 2 pages.

C. Kottler et al., Grating interferometer based scanning setup for hard x-ray phase contrast imaging, Review of Scientific Instruments, vol. 78, 034710, 2007, pp. 1-4.

Thomas Thuring, et al., Non-linear regularized phase retrieval for unidirectional X-ray differential phase contrast radiography, Optics Express, vol. 19, Issue 25, pp. 25545-25558, Optical Society of America 2011, issn: 10944087.

H.N. Cardinal and A. Fenster "An accurate method for direct dual-energy calibration and decomposition" Medical Physics, May-Jun. 1990; vol. 17, No. 3, pp. 327-341.

Chapman, D., Thomlinson, et al., "Diffraction enhanced x-ray imaging," Phys. Med. Biol., 42, 2015, (1997).

Bonse, et al., "An x-ray interferometer," Appl. Phys. Lett. 6(8), 155-156, (1965).

Ingal. V. N., et al., "X-ray plane-wave topography observation of the phase contrast from non-crystalline object," J. Phys. D 28(11), 2314-2317, (1995).

Wilkins, S. W., et al., "Phase-contrast imaging using polychromatic hard X-rays," Nature (London) 384(6607) 335-338, (1996).

Momose, A., et al., "Demonstration of X-ray Talbot interferometry," Jpn. J. Appl. Phys. 42, L866-L868, (2003).

Wietkamp, T., et al., "X-ray phase imaging with a grating interferometer," Opt. Exp. 13(16), 6296-6304, (2006).

Pfeiffer, F., "Phase retrieval and differential phase-contrast imaging with low-brilliance X-ray sources", Nature Phys. 2, 258-261, (2006).

* cited by examiner

PHASE RETRIEVAL FROM DIFFERENTIAL PHASE CONTRAST IMAGING

FIELD OF THE INVENTION

The application generally relates to digital x-ray imaging methods/systems, and more specifically, to methods and/or systems for artifact and/or noise reduction when acquiring multiple image information of an object (e.g., medical radiographic imaging) using phase contrast imaging techniques.

BACKGROUND

Conventional medical X-ray imaging devices rely on absorption properties of materials to provide information about interior structure of imaged objects. Such absorption type of imaging assumes non refractive X-rays penetrating the object under study. The contrast is produced because of the differences in the absorption cross section. While generally good contrast between highly attenuating (e.g., hard) and weakly attenuating (e.g., soft) materials is observed, the differentiation between soft-tissue materials can be difficult because of a low relative contrast. For example, the low-contrast soft tissue materials including, but not limited to vessels, cartilages, lungs, and breast tissues provide poor contrast in comparison to highly attenuating bone structures. The problem of soft-tissue imaging is addressed by interferometric X-ray imaging devices, which utilize the wave nature of X-ray radiation. Such imaging interferometers focus on measuring the refraction characteristics manifested in the process of X-rays passing through the object of study. In addition to absorption images of the object under study, these imaging interferometric devices can provide differential phase contrast images and dark-field images. We will refer to differential phase contrast imaging technique as DPCI. Differential phase contrast images contain information of X-ray phase shift properties through the object of study, e.g., similar to absorption imaging providing complementary knowledge of material properties. In contrast, dark-field images provide information about the local scattering of the object.

As an electromagnetic wave, the x-ray can be characterized by its frequency, amplitude, and phase. When an x-ray, as an electromagnetic wave, penetrates a medium, its amplitude is attenuated and phase is shifted. The refraction properties of X-rays penetrating the matter can be described by the complex index of refraction $$n=1-\delta+i\beta,$$

where the imaginary part $\beta$ contributes to the attenuation of the amplitude and the real part $\delta$ (refraction index decrement) is responsible for the phase shift. While the interferometer type of imaging devices can measure both $\beta$ and $\delta$ terms, the conventional ones can detect only $\beta$. It can be shown that $\delta$ (rad/cm units) is about $10^3$ to $10^4$ times larger than $\beta$ (1/cm units). Thus, the real part $\delta$ of the complex index of refraction provides a potential for imaging soft-tissue materials with higher contrast.

To date, several phase contrast imaging (PCI) techniques have been explored: 1) the interferometer technique, 2) the diffraction-enhanced imaging (DEI) technique, and 3) the free-space propagation technique. However, there are various practical problems associated with all three techniques. In the case of crystal interferometers and diffractometers, high temporal coherence (e.g., a high degree of monochromaticity) is required, which, in result, limits the application to a synchrotron radiation or a well defined monochromatic radiation source. In addition to the synchrotron source requirement, the use of multi-hole collimator in DEI limits the achievable spatial resolution and increases the acquisition time. The free-space propagation technique is limited in efficiency because of a requirement of high spatial coherence, which only can be obtained from an X-ray source with a very small focal spot size, or large propagation distance.

In addition, grating based differential phase contrast interferometry based on Talbot-Lau principles has been actively explored within the last decade. Such grating based differential phase contrast interferometry imaging devices can use a standard broadband X-ray tube when used together with a partially absorbing grating G0 (source grating), which can generate partially coherent X-ray radiation, and then the refraction characteristics of a scanned object can be detected via interference pattern, which is generated by a phase grating G1 and modulated onto an imaging detector (e.g., digital radiographic (DR) detector) by a partially absorbing grating G2.

Image acquisition procedures in the techniques described above typically require a plurality of X-ray exposures. Unanimously, all techniques described above require some of the geometrical parameters to be altered at each X-ray exposure. For example, a grating based inteferometry system requires one of the three gratings being translated (or stepped) with respect to the rest of the system at each X-ray exposure. Such an acquisition technique is referred to as phase stepping. The direction of the stepping (or scan) is typically perpendicular to trenches of the grating. The phase stepping acquisition for a grating based inteferometry system results in three images: 1) transmittance T image, 2) differential phase $\varphi$ image, and 3) dark-field DF image. The transmittance image represents a mean intensity measured by detector over a phase-stepping cycle. The differential phase image represents a gradient of X-ray phase shift occurred in the object in the direction of phase stepping (e.g., the direction of the grating's translation (e.g., the direction in which the G2 grating is stepped)). The dark-field image reproduces the intensity modulation observed during the phase stepping relative to the mean signal (or contribution of the scattering effects).

Information included in each of the respective images is significantly different from each other. As described above, the actual phase shift though the object, which is proportional to refraction index decrement $\delta$, is of a particular interest since the actual phase shift though the object can provide better soft-tissue contrast. To obtain such phase shift information, the differential phase image can be integrated along the differential direction (e.g., perpendicular to grating trenches and along phase stepping direction). Integration can correspond to dividing by the frequency in the spectral domain, and therefore low frequencies can be significantly amplified. Noise present in the differential phase data will get amplified along the direction of integration, which can result in severe streak artifacts, for example, oriented in the direction of integration.

Published US patent application 2013/0156284A1, "Regularized phase retrieval in differential phase-contrast imaging"; published paper, "Non-linear regularized phase retrieval for unidirectional X-ray differential phase contrast radiography" (Optics Express, V. 19, #25, pp. 25545-58, 2011); and published international application WO2012080125A1, "A method and a system for image integration using constrained optimization for phase contrast imaging with an arrangement of gratings" describe processes for solving problems of streak artifacts by regularizing the integration process of the differential phase data. These sources describe the regularization in the direction perpendicular to direction of integration of the differential phase, namely, one-dimensional regularization. One shortcoming of the described prior art is that in respective processes of eliminating streak artifacts, the regularization can also cause detail to be loss in the recovered phase. Detail loss can be highlighted for structures (e.g., edges) that are aligned with the direction of scanning and/or edges severely impacted by noise. Further, another shortcoming of the described prior art is that they do not account for a noise associated with non-uniformity of the grating structures (e.g., mostly manifested by non-uniformities in phase grating G1 and absorption grating G2).

Thus, there remains a need for phase retrieval methods, which can suppress streak artifacts without suppressing edges and can handle the non-uniformity of the grating structures in the phase image recovery.

SUMMARY OF THE INVENTION

An aspect of this application is to advance the art of medical radiographic imaging. Another aspect of the application is to provide methods and/or apparatus embodiments for digital radiographic phase contrast imaging.

Another aspect of this application is to address, in whole or in part, at least the foregoing and other deficiencies in the related art.

It is another aspect of this application to provide, in whole or in part, at least the advantages described herein.

It is another aspect of this application is to provide methods and/or apparatus to address and/or reduce disadvantages caused by the use of PCI imaging apparatus and/or methods using the same.

It is another aspect of this application is to provide x-ray interferometer devices and/or methods for differential phase contrast imaging based on the Talbot-Lau three-grating configuration. Another aspect of the application is to provide methods and/or apparatus embodiments for tuned or detuned PCI medical imaging.

It is another aspect of the application is to provide methods and/or apparatus embodiments for applications including but not limited to medical imaging, non-destructive testing, and/or security (e.g., national security).

It is another aspect of the application is to provide methods and/or apparatus embodiments for two dimensional regularization method with two dimensional edge enhancement features and/or two dimensional noise masks for extracting phase information impacted by noisy differential phase contrast data.

It is another aspect of the application is to provide methods and/or apparatus embodiments that can provide an image of phase contrast with reduced or suppressed noise; where the phase image can be extracted from differential phase data by 2D regularization procedure with additional 2D edge enhancement feature (e.g., where each dimension can be scaled individually) and/or noise dependent two dimensional masks applied as a weight to regularization parameter.

In accordance with one embodiment, the present invention can provide a method executed at least in part on a computer that can include retrieval of a phase contrast integrated image from basis images, including receiving a plurality of correlated basis images, where at least one of the basis images is a differential image; reconstructing an integrated image using at least one of the remaining basis images and the differential image; and presenting the images where at least one of the images is the reconstructed image.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other.

DESCRIPTION OF EXEMPLARY EMBODIMENTS

Figure 1:
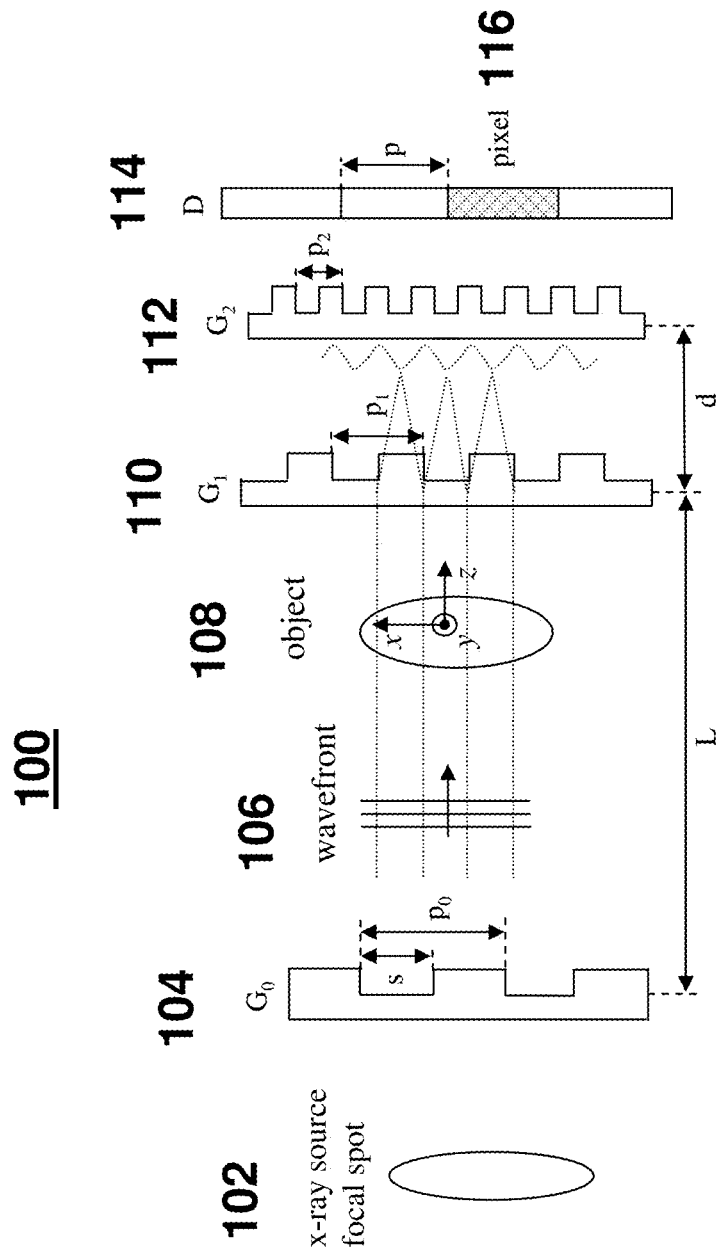
FIG. 1 is a diagram that shows schematics of an exemplary three-grating PCI system with a broadband X-ray source, three gratings G0, G1, and G2, and an X-ray detector.

The following is a description of exemplary embodiments of the invention, examples of which are illustrated in the accompanying drawings. Wherever possible, the same reference numbers will be used throughout the drawings to refer to the same or like parts.

For illustrative purposes, principles of the invention are described herein by referring mainly to exemplary embodiments thereof. However, one of ordinary skill in the art would readily recognize that the same principles are equally applicable to, and can be implemented in, all types of radiographic imaging arrays, various types of radiographic imaging apparatus and/or methods for using the same and that any such variations do not depart from the true spirit and scope of the application. Moreover, in the following description, references are made to the accompanying figures, which illustrate specific exemplary embodiments. Electrical, mechanical, logical and structural changes can be made to the embodiments without departing from the spirit and scope of the invention. In addition, while a feature of the invention may have been disclosed with respect to only one of several implementations/embodiments, such feature can be combined with one or more other features of other implementations/embodiments as can be desired and/or advantageous for any given or identifiable function. The following description is, therefore, not to be taken in a limiting sense and the scope of the invention is defined by the appended claims and their equivalents.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. Where they are used, the terms "first", "second", and so on, do not necessarily denote any ordinal or priority relation, but may be used for more clearly distinguishing one element or time interval from another.

Exemplary embodiments described herein for grating based interferometer devices and/or methods can be used for differential phase contrast imaging. Certain exemplary embodiments described herein provide regularization methods and/or apparatus for denoising and/or suppression of streak artifacts when recovering the X-ray phase image from X-ray differential phase contrast data.

In the description of this application, an edge aligned or oriented with a given direction can have a unit vector perpendicular to the edge normal. The edge normal is a unit vector in the direction of its gradient (maximum intensity change). For example, edge aligned with the x direction has maximum intensity change in the y direction.

In the description of this application, the vector $\vec{r}$ and scalar dimensions such as x, y, and z are used interchangeably, for example for a 2D case, $f(\vec{r})=f(x,y)$.

As described herein, DPCI can be performed by a number of different techniques. FIG. 1 shows schematics of a three-grating based DPCI system based on Talbot-Lau interferometry principles. For embodiments of the application described herein, one DPCI technique is chosen as a non-limiting representative example because other known or described techniques can be alternatively used. As shown in FIG. 1, a three-grating based DPCI system 100 can include a source grating G0 104, which can allow the use of a large incoherent X-ray source (e.g., standard broadband X-ray tube) 102 by creating an array of individually coherent line sources that can provide sufficient spatial coherence for the interferometric contrast. Alternatively, a microfocus X-ray source or synchrotron radiation source can be used instead of grating G0 and a large incoherent X-ray source. The phase grating G1 110 can operate as a beam splitter and divide the incoming beam primarily into the ±1 diffraction orders. These two ±1 diffracted beams can interfere and form a periodic interference pattern, which repeats itself at specific distances, called Talbot distances. Further, an analyzer grating G2 112 can be placed at one of such Talbot distances to modulate a moiré fringe pattern in the plane of X-ray detector D 114 placed directly behind G2 grating 112. Thus, the source grating G0 104 can generate a wave front 106 to pass though an object 108 to be imaged before impinging the phase grating G1 110. Such an exemplary DPCI imaging system 100 can be realized both for projection type of imaging and computed tomography (CT).

Data acquisition techniques in DPCI system 100 typically require a plurality of X-ray exposures. One of the acquisition techniques, which can be described here with no loss of generality, is called phase stepping. The phase stepping acquisition technique involves lateral displacement (e.g., in a form of stepping) of one of the gratings with respect to other gratings and X-ray detector 114 (e.g., stepping of G2 grating 112 along x axis) by a fraction of the respective grating pitch. As a result of such multiple displacements (e.g., steps) over a total pitch of the moving grating, each pixel 116 of the X-ray detector 114 can measure the periodic intensity curve (e.g., intensity sine or cosine curves). Reconstruction methods (for example, but not limited to, Fourier based) take advantage of such intensity oscillations (e.g., intensity curves) to extract the following basis images: 1) transmission image, 2) dark-field (or visibility) image, and 3) differential phase image.

For example, for detector pixels (i,j), an oscillation (or intensity) curve can be expressed by a Fourier series:

$$I_s(i, j, x_g) \approx a_s(i, j) + b_s(i, j)\cos\left(\frac{2\pi}{p_2}x_g + \phi_s(i, j)\right), \quad \text{equation (1)}$$

$$I_b(i, j, x_g) \approx a_b(i, j) + b_b(i, j)\cos\left(\frac{2\pi}{p_2}x_g + \phi_b(i, j)\right), \quad \text{equation (2)}$$

where a is an average value of modulated intensity, b is an amplitude of modulated intensity, and φ is a phase. Equation 1 can represent the intensity measurement with the object present, while Equation 2 can refer to the measurement without an object (e.g., reference scan). Applying inverse Fourier transformation the following basis images can be obtained:

1) transmission image:

$$T(i, j) = \frac{a_s(i, j)}{a_b(i, j)}, \quad \text{equation (3)}$$

2) dark-field (visibility) image:

$$V(i, j) = \frac{b_s(i, j)/a_s(i, j)}{b_b(i, j)/a_b(i, j)}, \quad \text{equation (4)}$$

3) differential phase image:

$$\left(\frac{\partial \varphi}{\partial x}\right)_{i,j} = \frac{p_2}{\lambda d_n}(\phi_s(i, j) - \phi_b(i, j)). \quad \text{equation (5)}$$

Figure 2:
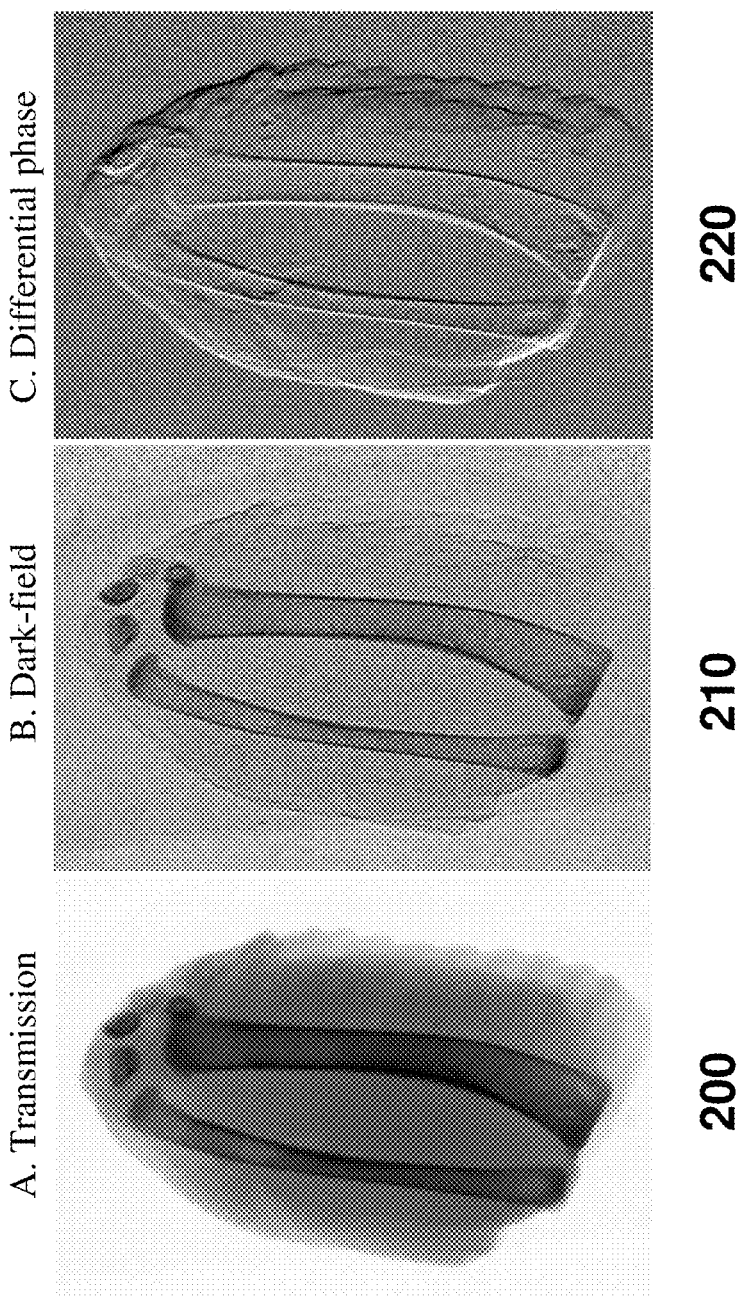
FIG. 2 is a diagram that shows an example of reconstructed basis images of chicken wing including (left to right) transmission, dark-field, and differential phase images.
Figure 3:
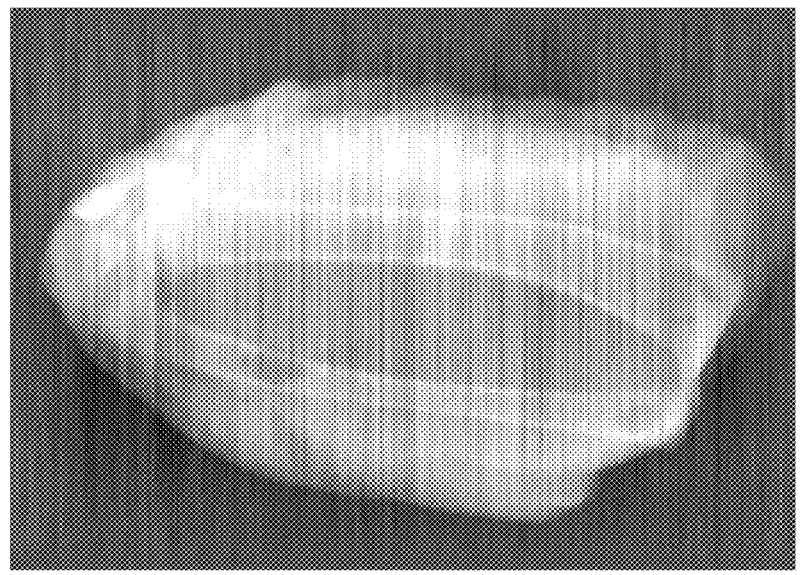
FIG. 3 is a diagram that shows an exemplary phase image obtained by direct integration of differential phase image in the differential direction (e.g., x-direction). The severe, horizontally oriented, streak artifacts are caused by noise present in the differential phase image.

To obtain an actual phase shift of X-rays through the imaged object 108 (e.g., object of interest), the differential phase image can be integrated along the differential direction. If the differential phase is denoted as ψ and the actual phase shift is denoted as φ, then the measured differential phase can be written as $$\varphi = \frac{\partial \phi}{\partial x} + \text{noise}, \quad \text{equation (6)}$$

where, without loss of generality, x was chosen as the differentiation direction, which, in the case of described phase stepping technique, can coincide with the direction of grating stepping. The actual phase shift ϕ will be a result of integration of equation (1) over x. The noise present in the differential phase data introduces randomly distributed offsets in the integration, which result in a streak-like artifacts propagating along direction of integration. FIG. 2 shows an example of reconstructed basis images of chicken wing. As shown in FIG. 2, transmission 200, dark-field 210, and differential phase 220 images for a chicken wing were obtained from an exemplary DPCI system. FIG. 3 is a diagram that shows an exemplary phase image obtained by direct integration of differential phase image in the differential direction (e.g., x-direction). As shown in FIG. 3, direct integration of the differential phase 220 can produce a phase image 300 severely affected by streak artifacts. Such horizontally oriented, streak artifacts are caused by noise present in the differential phase image 220. The streak artifacts can greatly compromise the diagnostic capability of the phase image 300. Although, all image information can be severely impacted by the artifacts, the information on the edges oriented in x-direction (e.g., in the direction of streak artifacts) can be particularly difficult to recover. Thus, it is important to address such streak-like artifacts.

Certain exemplary embodiments for devices and/or methods can be used to provide effective means for suppression or complete removal of such streak-like artifacts.

By measuring the differential phase from many different view angles, the principles of conventional absorption X-ray CT and/or tomosynthesis can be applied to generate phase contrast computed tomography (CT) volumes. Referring to DPCI system 100, different view angles can be obtained by rotating the object 108 around the y axis. Alternatively, DPCI system 100 can be mounted to a gantry to revolve around (e.g., completely or 180 degrees plus fan angle) the object 108. Volume image reconstruction is well known in the tomography arts and can be executed according to a number of algorithms that take 2-D projection images obtained at different angles as input and provide the reconstructed volume image data as output. These volume image reconstruction methods can include filtered back projection, iterative reconstruction and other similar techniques for combining the 2-D projection image data.

Figure 4:
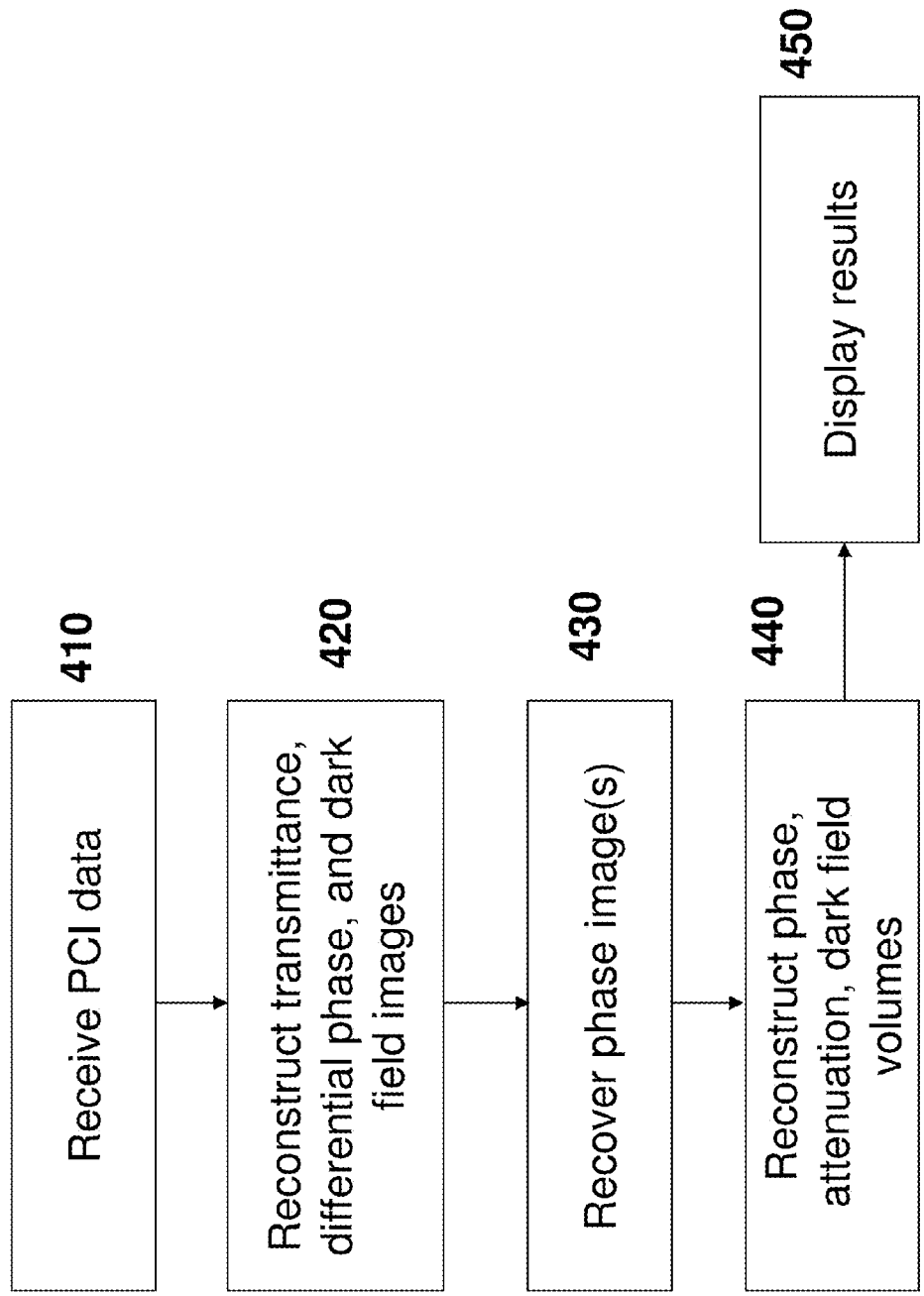
FIG. 4 is a flow chart that shows an exemplary embodiment of a method for phase retrieval in a phase contrast imaging system according to the application.

Referring to FIG. 4, a flow chart that shows an exemplary method for phase retrieval in a differential phase contrast imaging system according to embodiments of the application will now be described. The method for phase retrieval will be described using the exemplary DPCI system shown in FIG. 1; however, the method of FIG. 4 is not intended to be limited thereby. As shown in FIG. 4, after a process begins, PCI data can be received, for example, from either the PCI system 100 or from a storage file (operation block 410). The transmittance, visibility/dark-field, and differential phase images can be reconstructed from the PCI data (operation block 420). The phase image can be retrieved (e.g., recovered) from the differential phase image (operation block 430). Then, the phase, attenuation, and visibility/dark-field images (e.g., volumes) can be reconstructed (operation block 440). Further, the recovered phase, transmittance, visibility/dark-field, and differential phase images (and volumes) can displayed to the user (operation block 450). Alternatively, the recovered phase, transmittance, visibility/dark-field, and differential phase images (and volumes) can be stored for subsequent use or remotely transmitted for display, storage, modification or the like.

Recovery operations of the phase image from the measured differential phase image according to exemplary embodiments of the application will now be described. In descriptions that follow, it is assumed that the direction of the stepping (or scan) is in the x direction, which is perpendicular (orthogonal) to grating lines oriented in the y direction. However, no limitation to embodiments according to the application is intended thereby.

In certain exemplary embodiments according to the application, a variational model is used to recover the phase image from the measured noisy differential phase image. The principal is to reduce or minimize energy (objective) E function with respect to the phase image. The energy function for selected embodiments can be the sum of (i) a data fidelity term that measures how well the recovered phase fits the measured differential phase image and (ii) a regularization terms that enforces smoothness and/or prior knowledge on the recovered phase image.

$$E_0(\phi) = \mu J(\phi) + H_w(\phi, \psi), \quad \text{equation (7)}$$

where ϕ is the recovered phase image, ψ, is a measured differential phase image, J(ϕ) is the regularizing term, $H_w(\phi, \psi)$ is a weighted data fidelity term, and, μ is the regularization parameters, which can control trade-offs between regularizing and data terms.

A class of regularizers useful for practicing selected exemplary embodiments according to the application can control the smoothness via the gradient and higher order derivatives of the recovered phase image ϕ; these can include but are not limited to quadratic (Sobolev), total variation, Huber, generalized Gaussian Random Markov fields, higher order derivatives, and higher order total variation regularizers such as Total Generalized Variation. A second class of regularizers useful for practicing selected exemplary embodiments according to the application can include but are not limited to directional representation transformations such as wavelet, curvelet, shearlet, rigdelet, etc.

The weighted data fidelity term can spatially weight the data term based upon the uncertainty in the measured differential phase data. The weighted data fidelity term can act on the data term such that areas with low variance use less degree of smoothing and the areas with high variance use more smoothing. Examples of weighted data fidelity terms useful for practicing selected exemplary embodiments according to the application can include but are not limited to L1 and L2 norm of the difference between gradient of the recovered phase ϕ along differential direction and the measured differential phase ψ. For a one-dimensional grating system the weighted data fidelity is given by $$\iint w(x,y) |\nabla_x \phi - \psi|^p dxdy, \quad \text{equation (8)}$$

where w(x,y) is the uncertainty in the measured data and p=1 or 2. For a grating based PCI system, the variance of the differential phase is inversely proportional to the total number of photons used to generate the differential phase and the visibility of the measurements.

In one embodiment, the phase shift image ϕ can be obtained by reducing or minimizing the following objective function $E_1(\phi)$ with respect to ϕ:

$$E_1(\phi) = \mu \int |\nabla \phi| dxdy + \tfrac{1}{2} \int w(x,y) [\nabla_x \phi - \psi]^2 dxdy, \quad \text{equation (9)}$$

where the first term corresponds to a total variation regularizer and the second term corresponds to a L2 data fidelity term, $\nabla_x$ is a gradient along differential direction, and ∇ is a gradient operator applied in x and/or y dimensions. The regularization parameter µ controls the degree of smoothing and the amount of streak artifact reduction.

Although the degree of regularized smoothing can be weighted differently in each direction, smoothing in the direction perpendicular to streak artifacts (y direction) can be more efficient in removing streak artifacts than smoothing in the x direction. In order to recover the reduced streak artifact phase (or streak artifact-free phase) from the differential phase, the regularized solution to phase shift retrieval provides smoothing in x and/or y directions while the data term enforces the edges in the x direction. Thus, the edges in x direction are more likely to blur than the edges in y direction.

Figure 5:
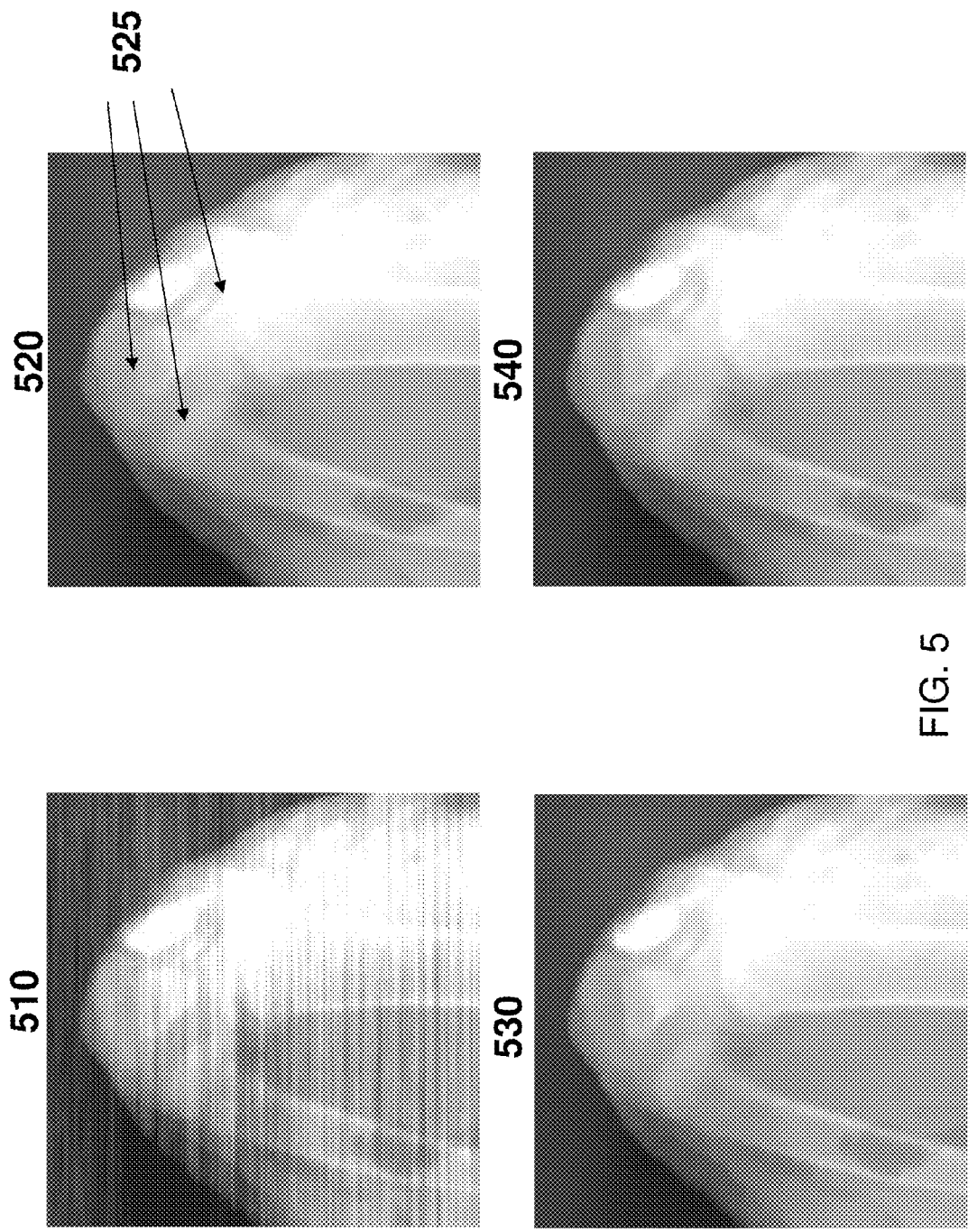
FIG. 5 is a diagram that shows examples of phase images recovered by exemplary regularization procedures including some with edge enhancement according to embodiments of the application.

Image 520 in FIG. 5 shows a result for a small region of interest (ROI) of regularized phase retrieval for chicken wing using Equation (9) with the data fidelity weight function w(x,y)=1. For comparison, image 510 shows a result of direct integration of differential phase that is severely affected by streak artifacts. Image 520 is a result of regularized phase retrieval without edge enhancement, and images 530 and 540 are the images of phase recovered by regularization procedure with edge enhancement options enabled according to selected exemplary embodiments. As observed for regularized phase retrieval image 520, the streaks are effectively removed; however some edges aligned with the scan direction (x-direction) are not fully recovered (see the arrows 525 pointing to the areas where the edges are washed out). The edges aligned to the direction of streak artifacts or scan direction can be the most difficult to recover due to the streaks generated from noise in the measured differential phase.

One shortcoming of the prior art is that in the process of eliminating streak artifacts, the regularization can also cause detail to be lost in the recovered phase. This loss of detail is especially highlighted for structures (e.g., edges) that are aligned to the direction of scanning. As previously described, the phase stepping procedure yields three images; transmittance, differential phase, and dark-field. Even though information carried by each of the images is significantly different; these images are highly correlated and contain redundancies that can be used in recovering the phase image according to embodiments of the application. For certain exemplary embodiments, the information contained in the transmittance and dark-field images can be used in recovering the phase image φ from the measured differential phase ψ using the following objective function:

$$E_2(\phi)=\mu_1 J(D^{1/2}\nabla\phi)+\mu_2 G(\phi,C)+H_w(\phi,\psi), \quad \text{equation (10)}$$

where J is correlation image driven regularizer, the weight matrix D is derived from the correlation image, $G(\phi,C)$ is a geometry (orientation) matching term that measures the alignment of the geometry of the phase and correlation image, C is a correlation image, which is a function of the transmittance and/or dark-field images, $H_w(\phi,\psi)$ is a weighted data fidelity term, and $\mu_1$ and $\mu_2$ are weighting scalars.

For certain exemplary embodiments, the correlation image can be used to guide the regularization of the recovered phase image and/or align the geometry of the recovered phase image with correlation image. The transmission T, dark-field DF (or visibility V), and differential phase ψ images are spatially correlated images containing different information about the same scanned object. The correlation image (C) is generated from transmittance and/or dark filed image and its intensity can be positively and/or negatively correlated with the phase image. Some examples of correlation images useful in practicing embodiments of the application include, but are not limited to C=T, C=1−T, C=−log (T), C=±DF, etc.

For certain exemplary embodiments, geometry information in the correlation image can be used to enforce similar geometry on the recovered phase. The geometry matching term G(φ,C) can measure the alignment of the geometry (level sets) of the correlation and phase image. Examples of geometry matching terms useful in practicing embodiments of the application include, but are not limited to $$\pm\iint\nabla\phi(x,y)\cdot\nabla C(x,y)dxdy=\mp\iint\phi(x,y)\text{div}(C(x,y)dxdy, \quad \text{equation (11)}$$

$$\pm\iint\nabla\phi(x,y)\cdot n_C(x,y)dxdy=\mp\iint\phi(x,y)\text{div}(n_C(x,y)dxdy, \quad \text{equation (12)}$$

where $$n_C = \frac{\nabla C}{|\nabla C|},$$

div( ) is the divergence operator, and the sign is dependent upon whether the correlation and phase images are positively or negatively correlated.

An example of a geometry matching functions that can handle positive and/or negative correlation is $$\iint|\nabla\phi(x,y)\cdot\nabla^\perp C(x,y)|dxdy, \quad \text{equation (13)}$$

where $\nabla^\perp$ is the tangent to the gradient vector.

The weight matrix specifies a correlation image structure dependent metric at point (x, y) that can be used to modify the amount or both the amount and direction of smoothing provided by the regularizer. The weight matrix can use the edge information in the correlation image to reduce smoothing across edges and/or encourage smoothing along edges in the phase image. Some examples of weight matrices that are useful in practicing embodiments of the application include, but are not limited to $$D=\text{diag}(g^2(\nabla_x C),h^2(\nabla_y C)), \quad \text{equation (14)}$$

$$D=\text{diag}(g^2(\nabla C)), \quad \text{equation (15)}$$

$$D=g(\nabla C)(\nabla^\perp C\cdot(\nabla^\perp C)^T+\lambda I), \quad \text{equation (16)}$$

$$D=g(\nabla C)\cdot n_C n_C^T+n_C^\perp n_C^{\perp T}, \quad \text{equation (17)}$$

where g and h are edge indicator functions, which is a strictly decreasing positive function, $$n_C = \frac{\nabla C}{|\nabla C|},$$

I is an identity matrix, $n_C^\perp$ is the tangent of $n_C$, λ is a scalar, and superscript T is the transpose. An example of edge indicator function is $$g(\nabla C)=\exp(-\alpha|\nabla C|^\beta), \quad \text{equation (18)}$$

where α and β are scalars.

In one embodiment, the phase shift image φ can be obtained by reducing or minimizing the following objective function $E_3(\phi)$ with respect to φ:

$$E_3(\phi)=\mu_1\int|D^{1/2}(x,y)\nabla\phi(x,y)|dxdy-\mu_2\int\nabla\phi(x,y)\cdot\nabla d(x,y)dxdy+1/2\lambda\int w(x,y)(\nabla_x\phi-\psi)^2 dxdy \quad \text{equation (19)}$$

where d=−log(T) is the density of transmittance image, D(x, y) is a 2×2 matrix that uses information in the density image to weight the total variation of the recovered phase. In this embodiment, the density and phase image are assumed to be positively correlated.

The phase image can be recovered by reducing or minimizing the energy (objective) E function with respect to the phase $\phi$ using gradient descent, conjugate gradient, and/or other minimization techniques. Alternatively, proximal gradient methods (e.g., forward backwards splitting, operator splitting) techniques can be used for reducing or minimizing the energy (objective) E function, where efficient techniques (e.g., minimization techniques) for the Poisson equation and primal dual formulations for the proximal solution can be used.

FIG. 5 shows results of using Equation 19 to recover the phase image of the chicken wing. In one exemplary embodiment, when the geometry matching term is included and the weight matrix D(x,y) is set to the identity matrix, one obtains the phase image 530. Phase image 540 in FIG. 5 shows the effect the weight matrix D(x,y) has on the recovery of phase image according to another embodiment. Phase image 540 was obtained by turning off the geometry matching term ($\mu_1$=0) and setting the weight matrix D(x,y)=diag($g^2(\nabla_y d)$, $g^2(\nabla_y d)$). As described earlier, the edges in the direction of streak artifacts or differential direction can be the most difficult to recover due to high noise from streaks and lack of edge information in differential direction. This result is clearly observed in phase image 520, where edges in x-direction are not obvious (see the arrows 525 pointing to the areas where the edges are washed out). Both the correlation driven regularizer $J_C(D_C^{1/2} \cdot \nabla \phi)$ and the geometry matching terms $G(\phi,C)$ effectively reduce or remove the streak artifacts in the phase image that are obtained by direct integration of differential phase 510, and restore the edges that were obscured by in Image 520 using Equation 9, to recover the phase images 530 and 540.

Additionally, the data term can be penalized by a spatially dependent (e.g., two-dimensional) weight. For a grating based PCI system, the variance of the differential phase is inversely proportional to the total number of photons used to generate the differential phase image and the visibility of the imaging system setup. For example, areas with low code values in the dark-field image contain higher noise in differential phase image, due to stronger scattering processes. Furthermore, the differential phase image can contain an additional noise associated with non-uniformities of phase (G1) and absorption (G2) gratings. For example, areas in differential phase image that correspond to the regions of over or under plating of absorption material (e.g., Au) in the G2 grating will contain higher noise due to sub-optimal duty cycle of the grating.

Figure 6:
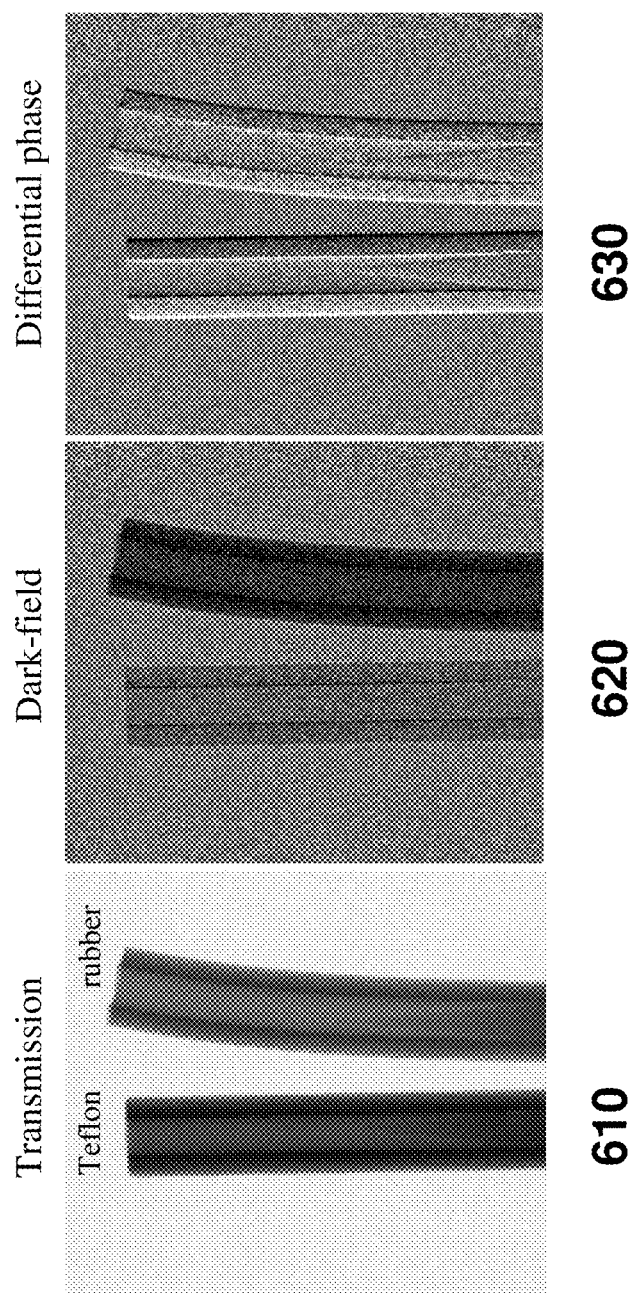
FIG. 6 a diagram that shows an example of noise in differential phase contrast imaging of two hollow tubes (Teflon and rubber).

FIG. 6 displays the transmittance 610, differential phase 620, and dark-field 630 images from the DPCI of two hollow tubes, one made of Teflon and another made from rubber. Compared to the Teflon tube, the rubber tube has lower code values in the dark-field 630 image, and as a result, has higher noise in the differential phase 620 image. This is especially noticeable around the areas where both tubes have the highest material thickness. Also, one can observe an elevated noise on right and left edges of dark-field 630 and differential phase 620 images. This is the noise associated with over plating of absorption material in the G2 grating.

Figure 7:
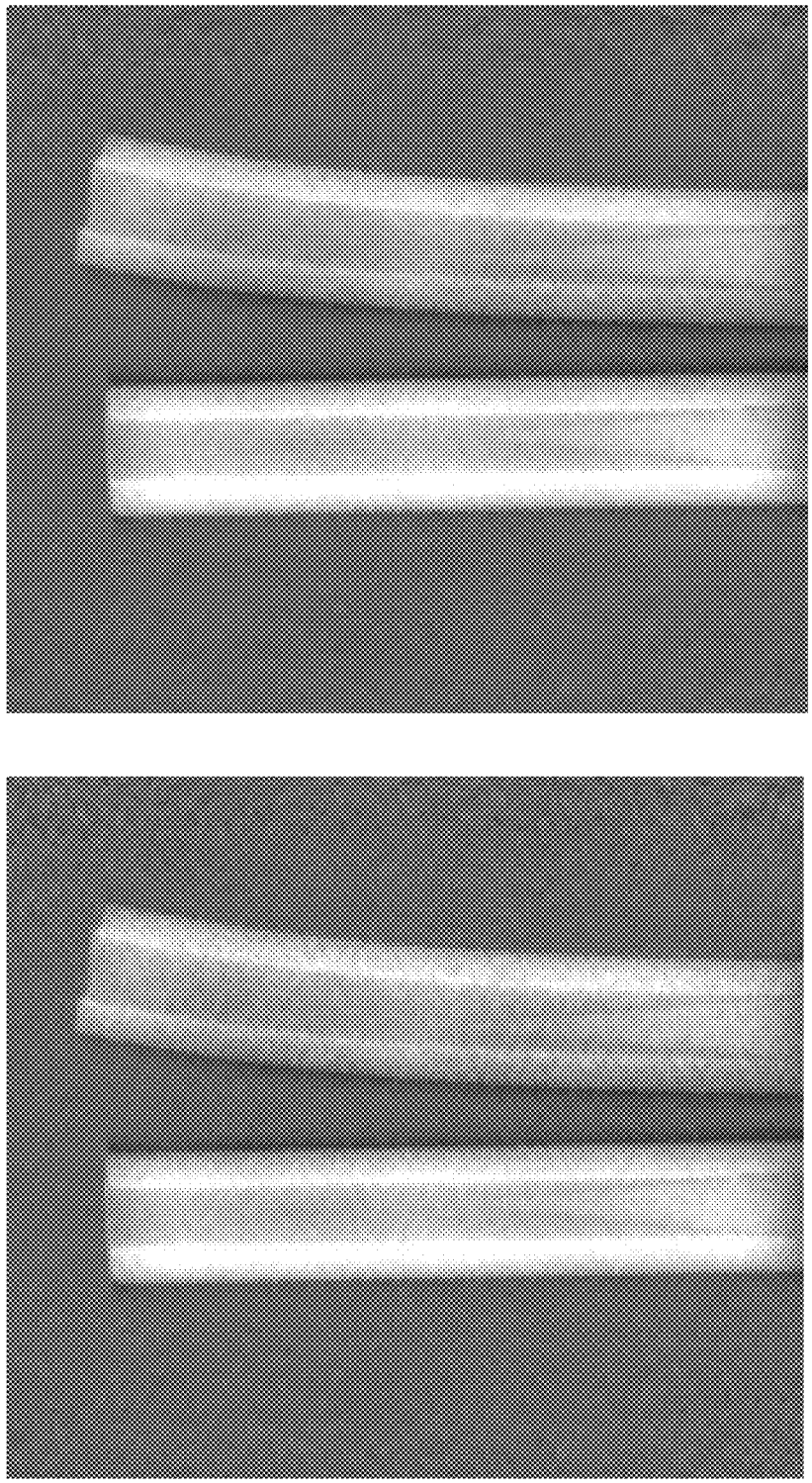
FIG. 7 a diagram that shows examples of phase images retrieved including some with spatial weighting of the regularizer term according to embodiments of the application.

FIG. 7 shows the results of using a spatially weighted data term for the recovery of the phase image from DPCI of two hollow tubes. The phase image 710 for non-weighted regularization 610 leaves higher noise in the thickest parts of the tubes (especially in the rubber tube) and on the left and right sides of the image. Weighting of the data term by the dark-field image and variance of the open field image generates a phase image 720 that can reduce the noise in the recovered phase of the rubber tube and/or reduce the noise on the left and right sides of the image.

One skilled in the art can realize that the information contained in the dark-field image can also be used instead of or along with the transmittance image in the process of recovering the phase image from the measured differential phase according to embodiments of the application. One skilled in the art can realize that discrete representation using matrix and vector notations could be used instead of the continuous representation used in this application to describe exemplary embodiments herein. Further, certain exemplary embodiments were described in terms of one-dimensional (1D) grating system, one skilled in the art can realize that embodiments can be extended to a two-dimensional (2D) grating system with the appropriate modification of the data terms $$\iint w_x(x,y)|\nabla_x \phi(x,y) - \psi_x(x,y)|^p dx dy + \iint w_y(x,y)|\nabla_y \phi(x,y) - \psi_y(x,y)|^p dx dy,$$

where $\nabla_x$ and $\nabla_y$ are the gradients in the x and y directions, $\psi_x$ and $\psi_y$ are the measured differential phase in the x and y directions, and $w_x$ and $w_y$ are weighting functions and p=1 or 2.

Further, although certain exemplary embodiments according to the application have been described in terms of 2D images, one skilled in the art can realize that embodiments herein can be extended to N-dimensional images, for example 3D volume.

Exemplary embodiments herein can be applied to digital radiographic imaging panels that use an array of pixels including direct detectors that use an X-ray absorbing photoconductor and a readout circuit or indirect detectors that use a separate scintillating screen, photodetectors and a readout circuit.

It should be noted that while the present description and examples are primarily directed to radiographic medical imaging of a human or other subject, embodiments of apparatus and methods of the present application can also be applied to other radiographic imaging applications. This includes applications such as non-destructive testing (NDT), for which radiographic images may be obtained and provided with different processing treatments in order to accentuate different features of the imaged subject.

Embodiments of radiographic imaging systems and/or methods described herein contemplate methods and program products on any computer readable media for accomplishing its operations. Certain exemplary embodiments accordingly can be implemented using an existing computer processor, or by a special purpose computer processor incorporated for this or another purpose or by a hardwired system.

Consistent with exemplary embodiments, a computer program with stored instructions that perform on image data accessed from an electronic memory can be used. As can be appreciated by those skilled in the image processing arts, a computer program implementing embodiments herein can be utilized by a suitable, general-purpose computer system, such as a personal computer or workstation. However, many other types of computer systems can be used to execute computer programs implementing embodiments, including networked processors. Computer program for performing method embodiments or apparatus embodiments may be stored in various known computer readable storage medium (e.g., disc, tape, solid state electronic storage devices or any other physical device or medium employed to store a computer program), which can be directly or indirectly connected to the image processor by way of the internet or other communication medium. Those skilled in the art will readily recognize that the equivalent of such a computer program product may also be constructed in hardware. Computer-accessible storage or memory can be volatile, non-volatile, or a hybrid combination of volatile and non-volatile types.

It will be understood that computer program products implementing embodiments of this application may make use of various image manipulation algorithms and processes that are well known. It will be further understood that computer program products implementing embodiments of this application may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with computer program product implementing embodiments of this application, are not specifically shown or described herein and may be selected from such algorithms, systems, hardware, components and elements known in the art.

While the invention has been illustrated with respect to one or more implementations, alterations and/or modifications can be made to the illustrated examples without departing from the spirit and scope of the appended claims. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only. The scope of the invention is indicated by the appended claims, and all changes that come within the meaning and range of equivalents thereof are intended to be embraced therein.

What is claimed is:

1. A method of reconstructing an integrated image from a differential image, the method comprising:
   receiving a plurality of correlated images each containing different image information about a same scanned object, the correlated images including a differential phase image, a transmission image, and a dark field image;
   reconstructing the integrated image by combining the differential phase image with only one of either the transmission image or the dark field image; and
   presenting the reconstructed integrated image.

2. The method according to claim 1, wherein the differential phase image is one-dimensional, the differential phase image is two-dimensional, or wherein the differential phase image is N-dimensional.

3. A method of reconstructing an integrated image from a differential image, the method comprising:
   receiving a plurality of correlation images, the correlation images including the differential image;
   reconstructing the integrated image using the differential image and at least another one of the correlation images; and
   presenting the reconstructed integrated image,
   wherein the step of reconstructing the integrated image includes determining an image that reduces an energy function, the energy function comprised of:
   i) a regularization term comprising a function of a recovered phase image and a weight matrix derived from at least one of the correlation images; or
   ii) a geometry matching function which aligns the geometry of the recovered phase image and at least one of the correlation images;
   or a combination thereof.

4. The method according to claim 1, wherein the reconstructed integrated image is obtained by determining an image that reduces an energy function comprised of:
   i) a regularization term comprising a function of a recovered phase image and a weight matrix derived from at least one of the correlation images; or
   ii) a geometry matching function which aligns the geometry of the recovered phase image and at least one of the correlation images,
   wherein the reconstructed integrated image is subjected to a data fidelity term.

5. The method according to claim 4, wherein the data fidelity term for the differential image is given by $$\sum_{\zeta=1}^{N} \int w_\zeta(\vec{r}^{\bar{\omega}}) |\nabla_\zeta \phi - \varphi_\zeta|^p d\vec{r}^{\bar{\omega}},$$

$w_\zeta(\vec{r}^{\bar{\omega}})$ is a weighting function, $\zeta$ is an index that corresponds to a differential dimension that can vary from 1, 2, ... N dimensions, $\phi$ is the recovered phase image, and wherein $\phi_\zeta$ is a measured differential image, and p=1 or 2.

6. The method according to claim 5, wherein the weighting function is related to an uncertainty in the measured differential image or measured differential data.

7. The method according to claim 6, wherein the uncertainty in the measured differential image comprises at least a variance of the measured differential image.

8. The method according to claim 5, wherein the regularization term is given by $$\int \Psi(D(\vec{r}^{\bar{\omega}}) \nabla \phi(\vec{r}^{\bar{\omega}})) d\vec{r}^{\bar{\omega}},$$

and wherein $\Psi$ is a regularization function and D is a weighting function in matrix form derived from at least one of the correlation images.

9. The method according to claim 8, wherein the regularization function $\Psi$ comprises one of quadratic functions, total variation functions, Huber functions, and generalized Gaussian Random Markov fields.

10. The method according to claim 8, wherein the weighting function matrix D is derived from edge information from at least one of the correlation images given by one of the following:

$$D=\text{diag}(g^2(\nabla_x C), h^2(\nabla_y C)), \quad \text{equation (14)}$$

$$D=\text{diag}(g^2(\nabla C)),$$

$$D=g(\nabla C)(\nabla^\perp C \cdot (\nabla^\perp C)^T + \lambda I),$$

$$D=g(\nabla C) \cdot n_C n_C^T + n_C^\perp n_C^{\perp T},$$

where g and h are strictly decreasing positive functions, $$n_C = \frac{\nabla C}{|\nabla C|},$$

I is an identity matrix, ∫ is a scalar, $n^\perp_C$ is a tangent of $n_c$, $\nabla^\perp$ is a tangent to the gradient vector, and wherein superscript T is a transpose.

11. The method according to claim 4, wherein the geometry matching term is given by one of the following:

$$\int \nabla \phi(\bar{r}^\omega) \cdot \nabla C(\bar{r}^\omega) d\bar{r}^\omega,$$

$$\int \nabla \phi(\bar{r}^\omega) \cdot n_c(\bar{r}^\omega) d\bar{r}^\omega, \text{ and}$$

$$\int |\nabla \phi(\bar{r}^\omega) \cdot \nabla^\perp C(\bar{r}^\omega)| d\bar{r}^\omega$$

12. The method according to claim 1, wherein the correlated images (C) are functions of transmission images (T) and dark-field images (DF) given by one of the following C=T, C=1−T, C=−log(T), C=±DF.

13. The method according to claim 1, wherein the correlated images are obtained for a plurality of different view angles around the same scanned object, and wherein the integrated image comprises a different integrated image from each of the plurality of different view angles.

14. The method according to claim 13, wherein volume image reconstruction methods are used to create a phase volume from the plurality of different integrated images.

15. A method of retrieving a phase contrast integrated image from basis images, the method comprising:
receiving a plurality of correlated basis images, the correlated basis images including a differential phase image, a transmission image, and a dark field image;
reconstructing the phase contrast integrated image by combining the differential image with only the transmission image and without the dark field image; and
presenting the reconstructed integrated image.

16. The method of claim 15, further comprising:
deriving the transmission image from a ratio of average modulated intensity of subject image data over average modulated intensity of reference image data, wherein the subject image data and the reference image data are obtained from a same differential phase contrast imaging system.

17. The method of claim 16, further comprising:
deriving a dark field image from a ratio of an amplitude of modulated intensity of the subject image data over an amplitude of modulated intensity of the reference image data.

18. The method of claim 1, further comprising:
deriving the transmission image from a ratio of average modulated intensity of image data of the scanned object over average modulated intensity of reference image data, wherein the image data of the scanned object and the reference image data are obtained from a same differential phase contrast imaging system.

19. The method of claim 18, further comprising:
deriving the dark field image from a ratio of an amplitude of modulated intensity of the image data of the scanned object over an amplitude of modulated intensity of the reference image data.

20. The method according to claim 18, wherein the differential phase contrast imaging system is configured to use a computer-readable medium in which a computer program for regularized phase retrieval in phase contrast imaging is stored, which computer program, when being executed by a processor, is adapted to carry out the method according to claim 1.

* * * * *

UNITED STATES PATENT AND TRADEMARK OFFICE
CERTIFICATE OF CORRECTION

PATENT NO. : 10,096,098 B2
APPLICATION NO. : 14/143183
DATED : October 9, 2018
INVENTOR(S) : Pavlo Baturin et al.

Page 1 of 1

It is certified that error appears in the above-identified patent and that said Letters Patent is hereby corrected as shown below:

In the Claims

Column 15, Claim 10, Line 1    Replace "I is an identity matrix, ∫ is a scalar, $\mathbf{n}_c^\perp$ is the tangent of $\mathbf{n}_c$," with -- I is an identity matrix, λ is a scalar, $\mathbf{n}_C^\perp$ is the tangent of $\mathbf{n}_C$, --

Signed and Sealed this
Thirtieth Day of July, 2019

Andrei Iancu
*Director of the United States Patent and Trademark Office*